United States Patent [19]

Doussain et al.

[11] Patent Number: 4,996,376
[45] Date of Patent: Feb. 26, 1991

[54] PREPARATION OF DINITROTOLUENES

[75] Inventors: Claude Doussain, Saint-Fons; Michel Gubelmann, Lyon; Jean-Michel Popa, Drancy, all of France

[73] Assignee: Rhone-Poulenc Chimie, Courbevoie, France

[21] Appl. No.: 425,930

[22] Filed: Oct. 24, 1989

[30] Foreign Application Priority Data

Oct. 24, 1988 [FR] France ................... 88 14228

[51] Int. Cl.$^5$ ........................... C07C 205/06
[52] U.S. Cl. ................................... 568/934
[58] Field of Search ........................... 568/934

[56] References Cited

U.S. PATENT DOCUMENTS

| | | |
|---|---|---|
| 2,012,985 | 9/1935 | Castner . |
| 2,400,287 | 5/1946 | Caesar . |
| 3,409,620 | 11/1968 | Ohman et al. . |
| 3,488,397 | 1/1970 | Hakansson et al. . |
| 3,714,272 | 1/1973 | Coon et al. . |
| 3,981,933 | 9/1976 | Cook et al. . |

FOREIGN PATENT DOCUMENTS

| | | |
|---|---|---|
| 2202056 | 3/1974 | France . |
| 485643 | 2/1970 | Switzerland . |
| 1436954 | 5/1976 | United Kingdom . |

Primary Examiner—Robert L. Stoll
Assistant Examiner—Valerie Fee
Attorney, Agent, or Firm—Burns, Doane, Swecker & Mathis

[57] ABSTRACT

Dinitrotoluenes are prepared by reacting mononitrotoluene(s) with nitric acid, in liquid phase, in the presence of an inorganic and acidic solid including at least one component selected from among orthophosphoric acid, pyrophosphoric acid, metaphosphoric acid, a metal dihydrogen phosphate, a metal hydrogen phosphate, a metal orthophosphate or a metal pyrophosphate, such metal cations having from 1 to 5 positive charges.

11 Claims, No Drawings

PREPARATION OF DINITROTOLUENES

BACKGROUND OF THE INVENTION

1. Field of the Invention:

The present invention relates to the preparation of dinitrotoluenes, and, more especially, to the preparation of dinitrotoluenes by reacting at least one mononitrotoluene with nitric acid, in liquid phase, in the presence of an acidic solid.

2. Description of the Prior Art:

Dinitrotoluenes, in particular 2,4-dinitrotoluene, mixed, if appropriate, with 2,6-dinitrotoluene, are useful intermediates in the production of toluene diisocyanate (TDI) for the ultimate preparation of various polyurethanes. 2,4-Dinitrotoluene is therefore produced industrially and on a very large scale. In such a context, the importance of an increase of a few percent in the degree of conversion and/or selectivity, for example, in any of the stages of the process is readily apparent.

2,4-Dinitrotoluene is conventionally produced by a liquid phase double nitration of toluene with a mixture of nitric acid and concentrated sulfuric acid. The concentration of the sulfuric acid employed for the second nitration (nitration of mononitrotoluene to dinitrotoluene) is typically on the order of 98%. Notwithstanding the problems of corrosion and the high cost of recycling large amounts of sulfuric acid, such process presents major other disadvantages, namely, the problematic nature of the removal of the catalyst, which is generally solved by repeated washings with water, and the requirement to concentrate the sulfuric acid before it is recycled, insofar as the reaction itself produces water.

Therefore, serious need continues to exist in this art for an efficient process for the preparation of dinitrotoluene, enabling the aforementioned disadvantages to be at least partially prevented.

SUMMARY OF THE INVENTION

Accordingly, a major object of the present invention is the provision of an improved process for the preparation of dinitrotoluenes which conspicuously ameliorates those disadvantages and drawbacks to date characterizing the state of this art.

Briefly, the present invention features reacting at least one mononitrotoluene with nitric acid, in liquid, phase, in the presence of an effective amount of an inorganic and acidic solid comprising at least one component selected from among orthophosphoric acid, pyrophosphoric acid, metaphosphoric acid, metal dihydrogen phosphates, metal hydrogen phosphates, metal orthophosphates and metal pyrophosphates derived from metals which form cations having from 1 to 5 positive charges.

DETAILED DESCRIPTION OF THE PREFERRED EMBODIMENTS OF THE INVENTION

More particularly according to the present invention, by the term "dinitrotoluene(s)" are preferably intended 2,4-dinitrotoluene, 2,6-dinitrotoluene and mixtures thereof.

By "nitrotoluene(s)" are intended p-nitrotoluene, o-nitrotoluene and mixtures thereof.

It will of course be appreciated, if the starting material is a mixture of ortho- and para-nitrotoluene, then a mixture of 2,4 and 2,6 isomers of dinitrotoluene will be obtained; if the starting material is para-nitrotoluene, 2,4-dinitrotoluene will be the only compound produced. The process according to the invention requires the presence of nitric acid. Concentrated forms of nitric acid are generally employed, with its concentration being greater than 90% and, preferably, ranging from 95% to 100%.

One of the essential characteristics of the process of the invention is the use of an inorganic and acidic solid.

By "solid" is intended a compound or a composition which is essentially insoluble in the reactants and the, intended organic final product and, where appropriate, essentially insoluble in an organic diluent and, preferably, also essentially insoluble in water.

Such a compound (or composition) of essentially inorganic nature can be in bulk qr dispersed forms, such as beads, pellets, extrudates and powders, the average dimensions of which will generally be the result of a compromise between the required activity, the cost and the particular separation methods selected.

By "acidity" are intended Lewis and/or Bronsted acidity.

The Bronsted acidity may be intrinsic in the compound (or in the composition) selected, or created by the presence of water.

Another essential characteristic of the process of the invention is the fact that the solid comprises at least one component selected from among orthophosphoric acid, pyrophosphoric acid, metaphosphoric acid, metal dihydrogen phosphates, metal hydrogen phosphates, metal orthophosphates and metal pyrophosphates derived from metals which form cations having from 1 to 5 positive charges.

By "phosphates" are intended the salts of a metal which forms cations having from 1 to 5 positive charges of orthophosphoric acid, in which at least one hydrogen atom has been replaced by a metal atom.

By "pyrophosphates" are intended the salts of a metal which forms cations having from 1 to 5 positive charges of pyrophosphoric acid, in which at least one hydrogen atom has been replaced by a metal atom.

Exemplary of metal orthophosphates comprising the composition of the solid of the invention, particularly representative are:

$Li_3PO_4$, $Ca_3(PO_4)_2$, $Mg_3(PO_4)_2$, $Cu_3(PO_4)_2$, $Zn_3(PO_4)_2$, $Mn_3(PO_4)_2$, $Co_3(PO_4)_2$, $Ni_3(PO_4)_2$, $BPO_4$, $CrPO_4$, $FePO_4$, $LaPO_4$, $AlPO_4$, $CePO_4$, $Ti_3(PO_4)_4$, $Ce_3(PO_4)_4$, $Si_3(PO_4)_4$, $Nb_3(PO_4)_5$.

Exemplary of metal monohydrogen phosphates comprising the composition of the solid of the invention, particularly representative are:

$CaHPO_4$, $Ti(HPO_4)_2$, $MgHPO_4$.

Exemplary of metal pyrophosphates comprising the composition of the solid of the invention, particularly representative are:

$Ca_2P_2O_7$, $Cu_2P_2O_7$, $Fe_4(P_2O_7)_3$, $TiP_2O_7$.

Among the various types of metal compounds set forth above, those advantageously used according to the invention are derived from metals which form cations having at least two positive charges and, preferably, from 3 to 5 positive charges.

To preferably carry out the process of the invention, a catalyst is used comprising at least one component selected from among orthophosphoric acid, pyrophosphoric acid, silicon orthophosphate, lanthanum orthophosphate and mixtures thereof. As indicated above, the solid may be in bulk or dispersed form. It may also be in the form of a solid support on which there is attached or dispersed at least one of the components mentioned above. The support may be selected from among oxides which are conventionally employed as catalyst supports, such as silicas, aluminas, titanium oxides, zirconium oxides and rare earth oxides.

Certain components of the solid of the present invention are common commercial products; other components are known per se and can be prepared by suitable methods described in the literature.

The amount of solid used according to the present invention is not critical and will generally depend on a compromise between the required activity, the cost of the solid and the various other operating conditions of the process.

In general, the amount of solid will be such as to provide a weight ratio of nitric acid to the solid ranging from 0.02 to 10. Advantageously, such ratio will range from 0.1 to 2.

The reaction between the mononitrotoluene(s) and nitric acid is conducted in liquid phase, and the molar ratio of nitric acid to the mononitrotoluene(s) may vary over wide limits. Preferably, such molar ratio will range from 0.1 to 10.

In general, a temperature of at least 40° C. is required to provide an acceptable rate of conversion and, above 100° C., interfering reactions are likely to arise, thus diminishing the advantage of a process of this type.

In a preferred embodiment of the invention, the liquid reaction mixture will also contain an organic diluent which is inert vis-a-vis the nitration reaction and stable under the operating conditions of the reaction. Moreover, the liquid diluent will preferably be such that the nitric acid and the mononitrotoluene(s) are as slightly soluble in the diluent as possible.

Exemplary of such diluents are:

(i) acyclic saturated halogenated hydrocarbons and, in particular, methylene chloride and 1,2-dichloroethane;

(ii) hydrocarbon derivatives containing chlorine and fluorine, more commonly referred to as Freon® and, in particular, F-113;

(iii) perfluorinated (poly)cycloalkanes containing from 5 to 12 carbon atoms, especially the compound derived from cyclohexane or methylcyclohexane by replacing all the hydrogen atoms by fluorine atoms, and perfluorodecalin;

(iv) mononitroalkanes containing from 1 to 4 carbon atoms; and (v) m-nitrochlorobenzene.

Perfluorodecalin or methylene chloride are advantageously used.

In this embodiment, 0.5 to 5 ml of diluent per g of solid introduced are preferably used, it being possible for other ratios to be observed for economic reasons and/or reasons associated with the actual design of the reactor which is selected to ensure a good liquid/solid contact.

The reaction is generally carried out in a device ensuring good liquid/solid contact, such as a stirred reactor or a reactor provided with a liquid circulation loop.

At the end of the time which is fixed for the reaction (or the desired residence time), the dinitrotoluene(s) is (are) recovered by any suitable means, for example by distillation, preceded by sedimentation or filtration of the catalyst, if appropriate.

In order to further illustrate the present invention and the advantages thereof, the following specific examples are given, it being understood that same are intended only as illustrative and in nowise limitative.

EXAMPLES 1 to 5:

Control Test a:

Into a 50-cm$^3$ three-necked round bottom flask fitted with a central stirrer and a condenser were introduced, at 25° C., 4 g of a solid whose nature, commercial origin and, where appropriate, pretreatment conditions are specified in the Table below, 8 cm$^3$ of perfluorodecalin (PFD; $C_{10}F_{18}$), 2.1 g (15 mmol) of paranitrotoluene and 1 g (16.1 mmol) of 100% nitric acid. The mixture was heated to 60° C. for 4 hours with stirring. The resulting mixture was filtered; the filtrate was washed with water.

The organic phase was then analyzed by gas phase chromatography.

The individual operating conditions and the results obtained are reported in the Table below, in which :

DC denotes the degree of conversion of p-nitrotoluene;

Y denotes the yield of 2,4-dinitrotoluene (DNT).

TABLE

| Example | Catalyst Nature | Source | Treatment | DC (%) | Y (%) |
|---|---|---|---|---|---|
| (a) | None | — | — | 27 | 76 |
| 1 | $Nb_3(PO_4)_5$ | CBMM | + | 34 | 90 |
| 2 | $CrPO_4$ | AV | + | 33 | 80 |
| 3 | $H_4P_2O_7$ | Fluka | None | 64.4 | 100 |
| 4 | $LaPO_4 \cdot 0.9\,H_2O$ | AV | + | 58.6 | 88 |
| 5 | $H_3PO_4$ | Fluka | None | 42 | 91 |

NB: CBMM: Brazilian company
AV: Alfa Ventron company
+: Heat treat at 400° C. in air for 3 hours

EXAMPLE 6:

Into a 100-cm$^3$ three-necked round bottom flask fitted with a central stirrer and a condenser (equipped with a bubble counter) were introduced at 25° C., 7.63 g of commercial phosphated silica (better known under its commercial name of "Catalyseur UOP"), predried for 4 hours at 220° C. in air and with a composition of $SiO_2/P_2O_5/H_2O = 26/61/13$, 6 cm$^3$ of perfluorodecalin (PFD) ($C_{10}F_{18}$), 2.74 g (20 mM) of paranitrotoluene (PNT) and 1.29 g (0.84 cm$^3$, 21.4 mM) of 100% nitric acid. The mixture was heated to 60° C. for 3.5 hours with good stirring. The phosphated silica was recovered by filtration on sintered glass and was washed several times with methylene chloride. The filtrate was washed with water. The organic phase was analyzed by gas phase chromatography. A PNT conversion (DC) of 60.6% and a selectivity (Y) for 2,4-DNT of 96.3% were observed. (The nature of 2,4-DNT was confirmed by GC coupled with mass spectrometry).

Control test b:

The procedure of Example 6 was repeated, but with half charges, in a cylindrical reactor fitted with magnetic stirring and in the absence of solid and of PFD. The results obtained were the following:

| DC (PNT) = 37% | Y (2,4-DNT) = 43%. |
|---|---|

EXAMPLE 7:

The procedure of Example 6 was repeated, but with half charges, in a cylindrical reactor fitted with magnetic stirring and for only 30 minutes. The results obtained were the following:

| DC (PNT) = 30% | Y (2,4-DNT) = 74%. |

EXAMPLE 8:

The procedure of Example 7 was repeated, but for 1.5 hours. The results obtained were the following:

| DC (PNT) = 39.6% | Y (2,4-DNT) = 85%. |

EXAMPLE 9:

The procedure of Example 7 was repeated, but for 3.5 hours. The results obtained were the following:

| DC (PNT) = 47.6% | Y (2,4-DNT) = 89%. |

EXAMPLE 10:

The procedure of Example 9 was repeated, but at 80° C. The results obtained were the following:

| DC (PNT) = 60% | Y (2,4-DNT) = 67%. |

EXAMPLE 11:

The procedure of Example 1 was repeated, but with Freon® 113 ($Cl_2FCCClF_2$) as diluent. The results obtained were the following:

| DC (PNT) = 39.9% | Y (2,4-DNT) = 86%. |

EXAMPLE 12:

The procedure of Example 1 was repeated, but with PNT as diluent. The results obtained were the following:

| DC (PNT) = 42.2% | Y (2,4-DNT) = 94%. |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a dinitrotoluene, comprising reacting at least one mononitrotoluene with nitric acid, in liquid phase, in the presence of a catalytically effective amount of an inorganic acidic solid including at least one component which comprises orthophosphoric acid, pyrophosphoric acid, metaphosphoric acid, a metal dihydrogen phosphate, a metal hydrogen phosphate, a metal orthophosphate or a metal pyrophosphate, said metal cations having from 1 to 5 positive charges.

2. The process as defined by claim 1, said acidic solid including at least one component comprising orthophosphoric acid, pyrophosphoric acid, metaphosphoric acid, a metal dihydrogen phosphate, a metal hydrogen phosphate, a metal orthophosphate or a metal pyrophosphate, said metal cations having at least 2 positive charges.

3. The process as defined by claim 2, said acidic solid including at least one component comprising orthophosphoric acid, pyrophosphoric acid, metaphosphoric acid, a metal dihydrogen phosphate, a metal hydrogen phosphate, a metal orthophosphate or a metal pyrophosphate, said metal cations having from 3 to 5 positive charges.

4. The process as defined by claim 1, said acidic solid including at least one component comprising orthophosphoric acid, pyrophosphoric acid, silicon orthophosphate, lanthanum orthophosphate or admixture thereof.

5. The process as defined by claim 1, said acidic solid comprising lanthanum phosphate.

6. The process as defined by claim 1, wherein the amount of said acidic solid present is such that the weight ratio of $HNO_3$ thereto ranges from 0.1 to 2.

7. The process as defined by claim 6, wherein the molar ratio $HNO_3$/mononitrotoluene(s) ranges from 0.1 to 10.

8. The process as defined by claim 1, carried out at a reaction temperature ranging from 40° C. to 100° C.

9. The process as defined by claim 1, carried out in the presence of an inert organic diluent.

10. The process as defined by claim 9, said inert diluent comprising perfluorodecalin.

11. The process as defined by claim 9, said inert diluent comprising methyleno chloride.

* * * * *